United States Patent [19]

Dhalla

[11] Patent Number: 5,002,179

[45] Date of Patent: Mar. 26, 1991

[54] PEN-LENS KIT

[76] Inventor: Alnoor Dhalla, 4707 Whitehorn Drive N.E., Calgary, Alberta, Canada, T1Y 1T8

[21] Appl. No.: 401,785

[22] Filed: Sep. 1, 1989

[30] Foreign Application Priority Data

Sep. 1, 1988 [CA] Canada .................................. 576512

[51] Int. Cl.$^5$ ............................................ A45G 11/04
[52] U.S. Cl. ........................................ 206/5.1; 206/38; 206/573
[58] Field of Search ...................... 206/5.1, 38, 573, 37

[56] References Cited

U.S. PATENT DOCUMENTS

| | | | |
|---|---|---|---|
| 2,575,431 | 11/1951 | Smith | 206/38 R |
| 2,940,589 | 6/1960 | Silverman | 206/5.1 |
| 3,326,358 | 6/1967 | Singleton | 206/5.1 |
| 3,822,780 | 7/1974 | Ulmer et al. | 206/5.1 |
| 3,880,278 | 4/1975 | Brown | 206/5.1 |
| 4,429,786 | 2/1984 | Hucal | 206/5.1 |

FOREIGN PATENT DOCUMENTS

| | | | |
|---|---|---|---|
| 607642 | 10/1960 | Canada | 206/5.1 |
| 685129 | 4/1964 | Canada | 206/5.1 |
| 13654 | 2/1974 | Japan | 206/5.1 |
| 506789 | 5/1939 | United Kingdom | 206/38 |
| 2085186 | 4/1982 | United Kingdom | 206/5.1 |

Primary Examiner—William Price
Attorney, Agent, or Firm—William R. Hinds; George H. Dunsmuir

[57] ABSTRACT

In general, contact lens cleaning kits include a plurality of separate elements which represent a carrying/storage problem. A simple, portable kit includes an elongated cylindrical casing defined by a base containing disinfectant or cleaning solution for receiving a lens carrier, which is dependent from a disc threaded into the top end of the base; a hollow cylindrical barrel mounted on the disc and carrying a removable syringe containing lens cleaning solution; and a cover connected to the syringe nozzle and to the barrel, the cover carrying a spring clip of the type used to hold a pen in a pocket and a small mirror on the spring clip to facilitate insertion of the contact lenses.

10 Claims, 1 Drawing Sheet

PEN-LENS KIT

BACKGROUND OF THE INVENTION

This invention relates to a contact lens kit, and in particular to a portable contact lens kit.

In general, the average contact lens user wears lenses from eight to ten hours each day. Typically the lenses are cleaned in the morning using squeeze bottles of saline solution and inserted into position, where they remain until the lenses are removed in the evening and again cleaned before being placed in a conventional lens case for overnight soaking. It is an increasingly common practice to carrying a contact lens kit or to have such a kit at the workplace for cleaning lenses during the day. The usual kits consist of a plurality of separate elements, including a lens carrier, disinfectant solution, neutralizing solution, saline cleaning solution and artificial tears. At the very least the kit should include a lens carrier and cleaning solution.

Contact lens carriers or kits are disclosed by U.S. Pat. Nos., 3,822,780, issued to Walter R. Ulmer et al on July 9, 1974; 3,880,278, issued to Frank E. Brown on Apr. 29, 1975 and 4,429,786, issued to Stephen J. Hucal on Feb. 7, 1984. The Hucal device comes closest to offering a solution to the problem tackled by the present inventor, namely the reduction of the number of separate elements carried by the contact lens user. The Hucal device provides two separate lens carriers and a plurality of containers or compartments for cleaning fluid.

The object of the present invention is to provide a relatively simple, compact, portable contact lens kit, which provides separate storage facilities for a pair of lenses and a cleaning solution container.

SUMMARY OF THE INVENTION

Accordingly, the present invention relates to a contact lens kit comprising elongated, tubular casing means, tubular cover means removably mounted at one end of said casing means, the combination of said cover means and casing means resembling a pen, said casing means being defined by a plurality of releasably interconnected elements including hollow base means for holding lens cleaning fluid, disc means for supporting a lens carrier in said base means, and barrel means, fluid container means at least partially in said barrel means, said barrel means being releasably connected to said cover means. The present invention also relates to a contact lens kit comprising elongated, tubular casing means;

tubular cover means removable mounted on one end of said casing means, the combination of said cover means and casing means resembling a pen, said casing means being defined by a plurality of releasably interconnected elements including hollow base means for holding lens cleaning fluid, disc means for supporting a lens carrier in said base means, barrel means and syringe means in said barrel means, said barrel means and syringe means being releasably interconnected and being releasably connected to said cover means.

BRIEF DESCRIPTION OF THE DRAWINGS

The invention will be described in greater detail with reference to the accompanying drawing, which illustrates a preferred embodiment of the invention, and wherein.

DESCRIPTION OF THE PREFERRED EMBODIMENTS

Figure 3:
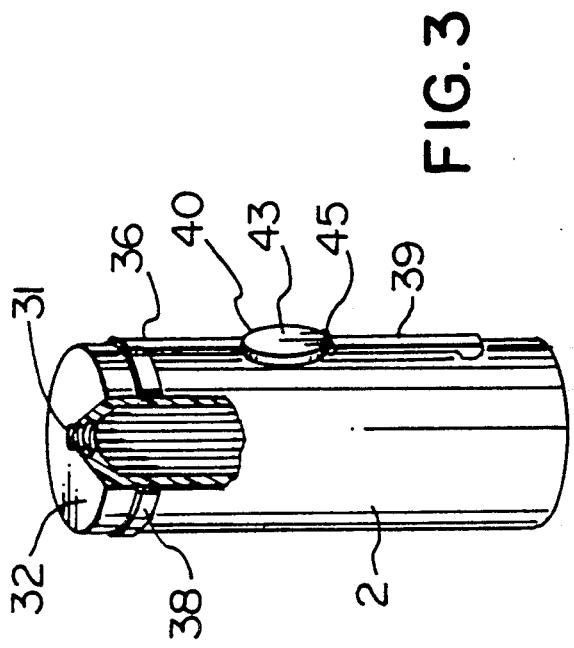
FIG. 3 is a partly sectioned, perspective view of a cover used on the kit of FIGS. 1 and 2.

With reference to the drawings, the contact lens kit of the present invention includes a pen-like casing generally indicated at 1, and a cover 2. The casing 1 is defined by a hollow cylindrical body or barrel 4 with a short base 5 on the bottom end thereof. A rod 7 with a threaded bottom end 8 extends downwardly from the closed bottom of the barrel 4 for carrying a disc 10. The disc 10 has a reduced diameter, threaded bottom end 11 for mounting the disc in the internally threaded top end 12 of the base 5. The lens basket 15 is a conventional article of the type described, for example in Canadian Patent No. 1,135,661, which issued to M. D. Thomas on Nov. 16, 1982.

The barrel 4 has an internally threaded top end 17 for mating with external threads 18 on a cylindrical syringe barrel 19. A ring or flange 20 on the open bottom end of the barrel 19 limits outward movement of a plunger 22, which is slidably mounted in the barrel 19. The plunger 22 includes a rod-shaped body 23, a disc-shaped, rubber head 25 and a handle 26 facilitating manual operating of the plunger 22. Even when fully extended, i.e. when the barrel 19 is full the outer free end of the handle 26 will not touch the closed bottom end of the barrel 4. Thus, the accidental ejection of cleaning fluid is prevented. The plunger 22 is used to force liquid through a tapering nozzle 28 on the conical top end 29 of the barrel 19. The nozzle 28 is externally threaded for engaging the frusto-conical, threaded sides of an opening 31 in the closed top end 32 of the cover 2.

Figure 1:
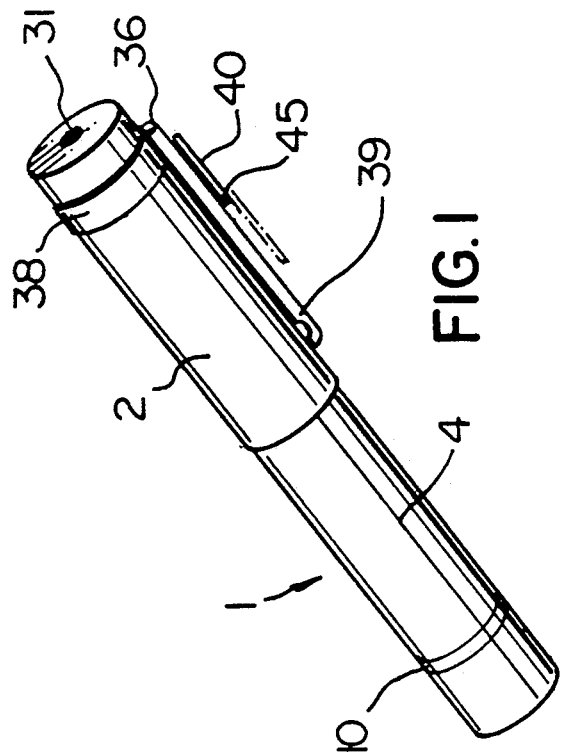
FIG. 1 is a schematic, perspective view of a contact lens kit in accordance with the present invention in the closed condition.
Figure 2:
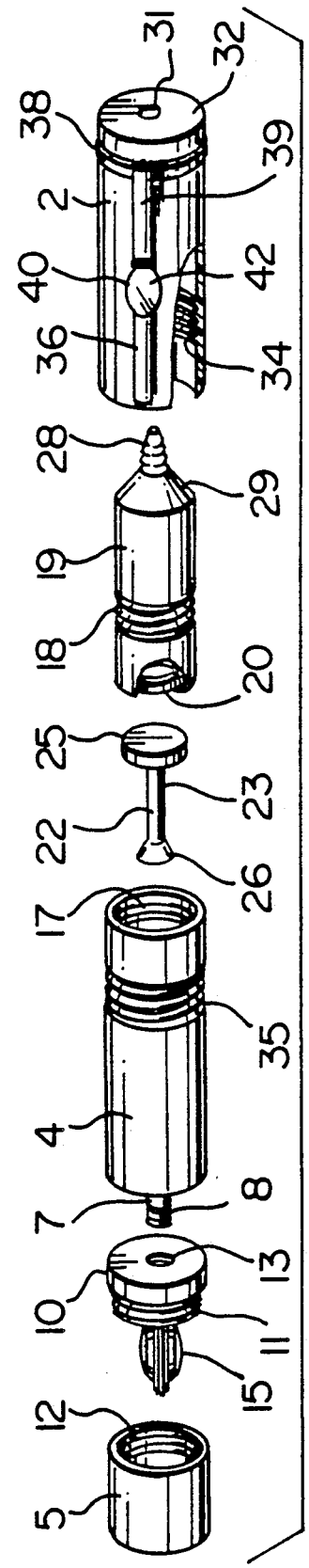
FIG. 2 is an exploded, partly sectioned, perspective view of the kit of FIG. 1.

Internal threads 34 in the cover 2 are used to connect the latter to the external threads 35 on the barrel 4, so that the device resembles one form of pen in the completely closed position. A pocket engaging clip 36 includes a ring 38 extending around the cover 2, and a spring stem 39 for attaching the clip to a pocket or holder top (not shown). A small mirror 40, with an inner reflective surface 43 and an outer plastic, non-reflective surface 42, is pivotally mounted on the stem 39 by means of a hinge 45 for rotation through 180° between the open position (FIG. 3) and the closed position shown in phantom outline in FIG. 1 and in solid lines in FIGS. 2.

In use, contact lenses (not shown) are stored in a saline solution in the base 5 of the casing 1. The lenses are easily removed by separating the base from the disc 10, on opening the lens basket 15. The base 5 is then reconnected to the disc 10. During insertion of the lenses, the normally protected mirror 40 is rotated 180° from the stored to the use position. When cleaning of the lenses is required, the cover 2 is first removed from the barrel 4, and then the syringe barrel 19 is removed from the barrel 4. By depressing the plunger 22, saline cleaning solution can be discharged in drops or in a steady stream from the syringe for lens cleaning.

The use of a syringe in the kit, ensures separation of the liquid in the base 5 normally carrying the lenses and the liquid used to clean the lenses. The liquid used to carry the lenses may contain bacteria, and consequently such liquid should not be issued to clean the lenses. The base 5 may contain either lens disinfectant or saline solution. The syringe can be refilled from a squeeze bottle using a commercially available rubber adapter (not shown) which is generally conical; with an accordion-like side wall.

What I claim is:

1. A contact lens kit comprising elongated, tubular casing means; tubular cover means removably mounted on one end of said casing means, the combination of said cover means and casing means resembling a pen, said casing means being defined by a plurality of releasably interconnected elements including hollow base means for holding lens cleaning fluid, disc means for supporting a lens carrier in said base means, barrel means and syringe means in said barrel means, said barrel means and syringe means being releasably interconnected and being releasably connected to said cover means.

2. A lens kit according to claim 1, wherein said syringe means includes externally threaded body means for mounting the syringe means in the barrel means, and externally threaded nozzle means for connecting the syringe means to said cover means.

3. A lens kit according to claim 2, wherein said barrel means includes a closed bottom end and threaded rod means on said bottom end for connecting the barrel means to said disc means, whereby the sides of the barrel means and said disc means and said base means define a smooth cylinder.

4. A lens kit according to claim 1, including clip means on said cover means for suspending the kit in the pocket of a user in the same manner as a pen.

5. A lens kit according to claim 4, including mirror means on said clip means for facilitating insertion into and removal of a lens from the eye of the user.

6. A contact lens kit comprising elongated, tubular casing means, tubular cover means removably mounted at one end of said casing means, the combination of said cover means and casing means resembling a pen, said casing means being defined by a plurality of releasably interconnected elements including hollow base means for holding lens cleaning fluid, disc means for supporting a lens carrier in said base means, and barrel means, fluid container means at least partially in said barrel means, said barrel means being releasably connected to said cover means.

7. A lens kit as claimed in claim 6 wherein said fluid container means is releasably interconnected with said barrel means.

8. A lens kit as claimed in claim 7 wherein said fluid container means includes externally threaded body means for mounting the fluid container means in the barrel means such that the fluid container means extends into said cover means.

9. A lens kit as claimed in claim 8 wherein said fluid container means includes externally threaded means for connecting the fluid container means to said cover means.

10. A lens kit according to claim 6 wherein said barrel means includes a closed bottom end and threaded rod means on said bottom end for connecting the barrel means to said disc means, whereby the sides of the barrel means and said disc means and said base means define a smooth cylinder.

* * * * *